United States Patent [19]

Blaschke et al.

[11] 4,415,487
[45] Nov. 15, 1983

[54] BIS-BETAINES, A PROCESS FOR THEIR PREPARATION, AND CLEANING AGENTS CONTAINING THESE COMPOUNDS

[75] Inventors: Günter Blaschke, Winhöring; Alwin Reng, Kelkheim; Jochen M. Quack, Eppstein, all of Fed. Rep. of Germany

[73] Assignee: Hoechst Aktiengesellschaft, Fed. Rep. of Germany

[21] Appl. No.: 439,729

[22] Filed: Nov. 8, 1982

[30] Foreign Application Priority Data

Nov. 19, 1981 [DE] Fed. Rep. of Germany ....... 3145733

[51] Int. Cl.³ .................... C07C 79/16; C11D 1/90; C11D 7/32
[52] U.S. Cl. .................... 252/546; 252/527; 252/528; 252/DIG. 5; 260/501.13; 564/294; 568/704; 568/712
[58] Field of Search .......... 252/546, 547, 527, DIG. 5, 252/528; 260/501.13; 564/294, 297, 298; 568/712, 704

[56] References Cited

U.S. PATENT DOCUMENTS

| | | | |
|---|---|---|---|
| 3,028,415 | 4/1962 | Nordgren | 260/465.5 |
| 3,366,671 | 1/1968 | Cowen et al. | 260/501.13 |
| 3,615,797 | 10/1971 | Ohtsuka et al. | 106/278 |

*Primary Examiner*—John E. Kittle
*Assistant Examiner*—Mukund J. Shah

*Attorney, Agent, or Firm*—Connolly & Hutz

[57] ABSTRACT

Bis-betaines of the formula

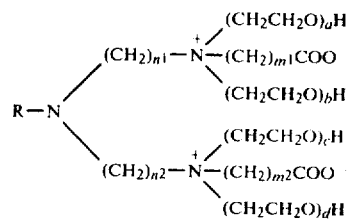

in which

R denotes a saturated or an olefinically unsaturated hydrocarbon radical which has 1 to 3 double bonds and 8 to 22 carbon atoms, $n^1$ and $n^2$ represent an integer from 2 to 3, and $n^1$ and $n^2$ can be identical or different, $m^1$ and $m^2$ represent an integer from 1 to 4, and $m^1$ and $m^2$ can be identical or different, and a, b, c and d, which are identical or different, each is a number from 1 to 5, but the sum (a+b+c+d) should be at most 10.

The compounds are prepared from primary amines of the formula $RNH_2$, by dicyanoalkylation, hydrogenation, ethoxylation and reaction with alkali metal salts of ω-halogenocarboxylic acids. They are suitable for formluating cosmetic and industrial cleaning agents.

4 Claims, No Drawings

BIS-BETAINES, A PROCESS FOR THEIR PREPARATION, AND CLEANING AGENTS CONTAINING THESE COMPOUNDS

To remove exogenous and endogenous soiling from skin and hair, anionic, cationic, amphoteric or non-ionic compounds are customarily used, on their own or in the form of combinations within these groups. The majority of commercially available body and hair cleaning agents are prepared using anionic surfactants of the soap, alkyl-sulfate, alkyl ether sulfate, sulfosuccinate, secondary alkyl-sulfonate, α-olefinsulfonate, acylaminopolyglycol ether sulfate or sarcoside type. These substances have a number of disadvantages when used under practical conditions. For example, hair is frequently too severely degreased, considerably impairing the combability of wet and dry hair and, in addition, adversely influencing the handle of the hair. When the customary surfactants are used in body cleaning agents, such as, for example, hand washes or shower baths, the over-strong cleaning action causes the skin to become dry and taut. At the same time, it is observed that due to the adsorption of the anionic surfactants the skin feels unpleasant and "tacky" after application. Attempts have already been made to overcome these disadvantages by adding cationic surfactants, but the formation of electrically neutral salts between anionic and cationic surfactants frequently brings about turbidities or precipitations in the formulations. The addition of substances which are polymeric and cationic also frequently causes problems due to reduced foam formation and too high an adsorption on the hair, which leads to an unpleasant accumulation effect.

Even amphoteric surfactants having a betaine group in the molecule have been tried, either on their own or combined with anionic surfactants.

German Auslegeschrift No. 1,249,433 describes, for example, the use of alkylbetaines in cleaning agents, while amidoalkylbetaines of the formula $R^1CONH.(CH_2)_x.N^+R^2R^3.(CH_2)_y.COO^-$, in which $R^1$ is the alkyl radical of a fatty acid have been recommended as skin-compatible bath additives, in German Auslegeschrift No. 1,172,802, and as germicidal hair washes which do not irritate the eyes, in German Auslegeschrift No. 1,062,392. However, the surfactant action of these mono-betaines is inadequate. In addition, the alkylbetaines, for example, have poor compatibility with the mucous membrane of the eye and even that of the amidoalkylbetaines is still not optimal.

The object of the invention is, accordingly, to provide new and improved betaines which do not irritate the skin and the mucous membrane of the eye, a process for their preparation and hair shampoos and cosmetic cleaning agents which contain these betaines. In particular, such betaines, when used in hair or body cleaning agents, should bring about a softening effect, desired by the consumer, while retaining the remaining favorable properties.

To achieve this object, the invention provides bis-betaines of the general formula

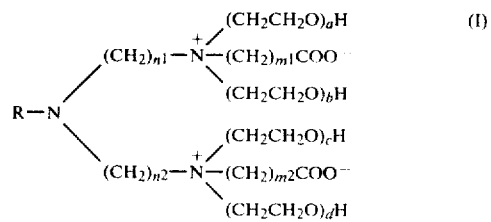

in which

R denotes a saturated or an olefinically unsaturated hydrocarbon radical which has 1 to 3 double bonds and 8 to 22 carbon atoms, $n^1$ and $n^2$ represent an integer from 2 to 3, and $n^1$ and $n^2$ can be identical or different, $m^1$ and $m^2$ represent an integer from 1 to 4, and $m^1$ and $m^2$ can be identical or different, and a, b, c and d, which are identical or different, each is a number from 1 to 5, with the proviso that the sum (a+b+c+d) should be at most 10.

In these bis-betaines according to the invention, of the formula I, the radical R has 8 to 22 carbon atoms, it can be saturated or unsaturated with 1 to 3 olefinic double bonds, and it can be straight-chain or branched. These alkyl or alkenyl radicals, which originate in the primary starting amine in the preparation of bis-betaines according to the invention, are frequently mixtures or fractions of particular chain lengths, preferably with the chain distribution of the radicals of natural fatty acids, such as, in particular, the coconut, tallow or palm kernel fatty acid, from which these starting amines can be obtained via the path of nitrile-hydrogenation or ammonolysis of the corresponding alcohols. The alcohols used for preparing the primary amines by means of ammonolysis can be not only fatty alcohols but also those which have a straight or branched chain from the Ziegler process (alcohols obtained by the growth reaction from ethylene) or from the oxo synthesis.

To prepare compounds according to the invention, such a primary amine of the formula $RNH_2$ (II) in which R has the abovementioned meaning is first reacted with 2 moles of at least one reactive nitrile of 2 to 3 carbon atoms (including the CN group) to give a compound of the general formula

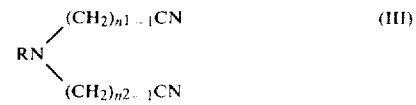

in a dicyanoalkylation reaction. This reaction is known, for example from U.S. Pat. No. 3,028,415. The reaction can be carried out not only with acidic but also with basic catalysis, with the aid of solvents, such as water or low-molecular weight alcohols, unpressurized or under an elevated pressure, in a continuous or discontinuous manner. Acidic catalysts mentioned are acetic acid, phosphoric acid, hydrochloric acid and other mineral acids (U.S. Pat. No. 3,615,797, U.S. Pat. No. 3,028,415 and German Offenlegungsschrift No. 1,941,913), and basic catalysts which have been recommended are sodium hydroxide, potassium hydroxide, alkali metal alcoholates, trimethylbenzylammonium hydroxide and morpholine (Kirk-Othmer, Encyclopedia of Chemical Technology, 1965, Volume 6, page 634 et seq.; and H. A. Bruson "Cyanoethylation", Organic Reactions, 5, 1949, page 79 et seq., published by John Wiley and Sons, New York). Water or lower alcohols, such as methanol, ethanol, isopropanol or mixtures of the same, are added as co-catalysts or also as solubilizers in amounts of 1 to 20% by weight. The dicyanoalkylation is carried out under atmospheric pressure or a slight to medium overpressure of 1 to 20 bar, optionally in the presence of an inert gas, at temperatures of 60° to 150° C. The cyanoalkylating agent, preferably acrylonitrile or chloroacetonitrile, is used stoichiometrically or in up to four-fold excess.

The dicyanoalkylation product (III) thus obtained is then reduced in the presence of hydrogen to give a compound of the formula

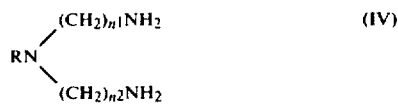

which is then condensed with ethylene oxide to give a compound of the formula

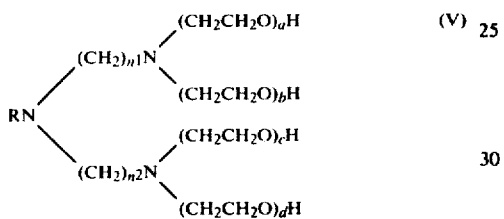

The two reactions are likewise known for obtaining the compounds at issue (cf. U.S. Pat. No. 3,615,797, already mentioned above). The reduction is carried out by means of Raney nickel or Raney cobalt or by means of supported nickel or cobalt catalysts, namely with the use of 1 to 10% by weight of catalyst, preferably 1 to 5% by weight, under pressures of 50 to 200 bar of hydrogen and at temperatures of 60° to 150° C.; the time for this reaction is about 1 to 5 hours.

The ethoxylation reaction is carried out in pressure vessels, namely at an elevated temperature within a range of 110° to 170° C. and under an elevated pressure of 1 to 5 bar. A catalyst is not required if, preferably, only one ethylene oxide unit is to be added per chain. If a catalyst is used, ethylene oxide chains which contain more than one unit are preferentially obtained. 4 to 10 moles of ethylene oxide are used per 1 mole of compound IV in the reaction, preferably 4 to 5 moles. In the addition, the ethylene oxide can be diluted with an inert gas.

The ethylene oxide addition product thus obtained is finally reacted in an aqueous solution to give the bis-betaine of the formula I, namely in a way which is in itself known with at least one alkali metal salt of an ω-halocarboxylic acid of the formula $X(CH_2)_{m^1}(m^2)COOH$. The alkali metal salts, and, in particular, the sodium salts, of chloroacetic acid, chloropropionic acid, bromoacetic acid and of chloro-n-butyric acid may be mentioned as preferred. If appropriate, halocarboxylic acid and alkali metal hydroxide can be added separately, the salt forming in situ. This reaction is carried out at a temperature of 80° to 100° C. with a 5 to 10% excess of halocarboxylic acid. Advantageously, bis-betaines according to the invention, of the formula I, are prepared as 30 to 40% by weight strength aqueous formulations by suitably adjusting the water content in the final reaction stage.

Bis-betaines according to the invention, as defined in the abovementioned formula I, are highly suitable for use in cosmetic cleaning agents, i.e. body cleaning agents such as foam baths, shower baths, foot and hand washes or intimate washes and also in hair washes. On use in body cleaning agents a marked improvement in the way the skin feels after the application is achieved, and on use in shampoos there is an improvement in the combability not only of dry but also of wet hair with a simultaneous softening effect, which manifests itself in the hair by a pleasant handle.

Bis-betaines according to the invention can be used in such liquid, pulverulent or aerosol-type cosmetic cleaning agents, in particular in hair washes, not only alone but also combined with anionic, cationic, non-ionic and amphoteric surfactants which are customarily used in such agents. Examples of anionic surfactants which are suitable for this purpose are soap, fatty alcohol sulfates, alkyl ether sulfates, fatty acid condensation products, such as taurides, methyltaurides and sarcosides, also α-olefinsulfonates, hydroxyalkanesulfonates, secondary alkanesulfonates, amide ether sulfates and alkylbenzenesulfonates. Examples of compounds which can be used as non-ionic surfactants are polyglycol monoalkyl ethers and monoesters, amine oxides and ethylene oxide/propylene oxide condensation products. In addition, the combination with other amphoteric surfactants, such as alkylbetaines, alkylamidobetaines, imidazoline derivatives or sulfobetaines, is also possible. Finally, bis-betaines according to the invention can also be used admixed with cationic surfactants, such as cetyltrimethylammonium chloride, cetyltrimethylammonium bromide, pentaoxyethylstearylammonium chloride, quaternized ether-amines or polymeric quaternary ammonium compounds. Further additives which are used in an otherwise customary manner in cosmetic cleaning agents can be combined with the bis-betaines. Examples of these additives are viscosity-increasing or viscosity-decreasing compounds such as cellulose ethers, electrolytes, such as, for example, sodium chloride or ammonium chloride, fatty acid polyglycol esters, alkanolamides, magnesium aluminum silicates, polyglycols, glycerol and ethanol. Further additives which can be used are perfume oils and special fragrances, antiseptic agents, dandruff-removing or fungus-killing agents, superfatting agents, preservatives, dyestuffs and nacreous substances. Filler and carrier substances which are customarily used, such as highly disperse and amorphous silica, sodium sulfate, magnesium aluminum silicate, starch derivatives and the like, can also be used in the processing to give pulverulent formulations. Finally, customary propellant gases can also be admixed in the case of aerosol-type formulations. The control of the pH value desired can be effected with inorganic or organic acids or alkalis.

Further, bis-betaines according to the invention are also suitable for formulating industrial cleaning agents, i.e. foam cleaners for textile surfaces, such as carpet cleaners, or, in particular, cleaning agents for hard surfaces, such as, for example, washing-up liquids, bottle-rinsing agents, floor cleaners, sanitary cleaners or so-called all-purpose cleaning agents. Bis-betaines according to the invention are finally suitable as agents for washing textiles. In these possible applications, too, the abovementioned anionic, cationic, non-ionic or amphoteric surfactants can be admixed. Chelating agents and, if appropriate, also dispersions of plastics can be added as customary auxiliaries to industrial cleaning agents. Other additives which are customary for this purpose are bleaching agents, chlorine donors or other disinfectants. To improve the abrasion effect, suitable additives are chalk, highly disperse amorphous silica, phosphates and plastics. To improve the fat- and soil-solubilizing properties, solvents such as universal spirit or isopropyl alcohol or other cleaning-promoting agents can also be added. Finally, washing agents contain customary builder substances.

A particular application advantage of using bis-betaines in industrial and cosmetic cleaning agents is their stability in the acid and alkaline pH range. For example, it is possible to prepare shampoos which have an acid pH value and a long shelf life without, as is the case with customarily used anionicalkylsulfates or alkyl ether sulfates, decomposition by hydrolysis occurring.

The content of bis-betaines according to the invention in such formulations is usually 0.5 to 40% by weight.

The examples which follow are intended to illustrate the invention in more detail:

PREPARATION EXAMPLES

EXAMPLE 1

670 g of coconut fatty amine (mole % composition in respect of the R radicals: $C_8$ 6%, $C_{10}$ 6%, $C_{12}$ 54%, $C_{14}$ 18%, $C_{16}$ and $C_{18}$ 8%), 68 g of water, 34 g of methanol and 14 g of concentrated acetic acid were heated to 60° C. in a 2 liter four-necked flask equipped with a reflux condenser, thermometer, stirrer and metering vessel. 373 g of acrylonitrile were added dropwise in the course of one hour, and the mixture was stirred for a further 24 hours at 75° C. under reflux. The mixture was then neutralized with 13 g of NaOH and 120 g of water, the wash water was separated off, and the product was freed from residual water and solvent in vacuo. 1,000 g of coconut-aminodipropionitrile (yield: 95.9%) were obtained.

A 5 liter autoclave was filled with 2,020 g of coconut-aminodipropionitrile, 3 g of supported cobalt catalyst (support: kieselguhr) and 300 ml of liquid ammonia. The hydrogenation took 3 hours under 150 to 180 bar of $H_2$ and at 110° to 140° C. After the catalyst had been filtered off, 2,010 g of a product which contained 85 to 95% of bis-(3-aminopropyl)-coconut-amine were obtained.

954 g of bis-(3-aminopropyl)-coconut-amine were heated with stirring to 130° C. in a 2 liter pressure vessel equipped with a thermometer, stirrer and an inlet and outlet for ethylene oxide. 667 g of ethylene oxide were added under a pressure of 1 to 3 bar. The increase in weight after a reaction time of 3 hours corresponded to a condensation product of the triamine with 4 to 5 moles of ethylene oxide. 1,605 g of this ethoxylate (99%) were obtained.

244 g of this bis-(3-aminopropyl)-coconut-aminoethoxylate and 622 g of water were initially introduced into a 2 liter reaction vessel and heated with stirring to 90° C. 113 g of sodium chloroacetate were added at this temperature within 1 hour, and the mixture was stirred for a further 12 hours at 95° C. The bis-betaine according to the invention was obtained in 970 g of a 30% by weight strength aqueous solution.

EXAMPLE 2

670 g of laurylamine ($C_{12}$-fraction: 73 mole %, and $C_{14}$-fraction: 23 mole %) were reacted in the manner already described in Example 1 with 373 g of acrylonitrile in 68 g of water, 34 g of methanol and 14 g of concentrated acetic acid. After neutralization and washing, 1,000 g of laurylaminodipropionitrile were obtained.

The hydrogenation of 2,020 g of the dipropionitrile produced bis-(3-aminopropyl)-laurylamine in a quantitative yield. 954 g of this triamine were condensed with 640 g of ethylene oxide. 1,590 g of bis-(3-aminopropyl)-laurylamine ethoxylate (99%) were obtained. 257 g of this ethoxylate and 676 g of water were reacted with 116.5 g of sodium chloroacetate. The bis-betaine was obtained in 1,070 g of a 30% strength aqueous solution.

EXAMPLE 3

844 g of myristylamine were reacted at 75° C. with 373 g of acrylonitrile in 68 g of water, 34 g of methanol and 14 g of concentrated acetic acid. 1,164 g of myristylaminodipropionitrile were obtained. 2,052 g of the dipropionitrile were hydrogenated in the manner of Example 1 using a cobalt catalyst. 2,045 g of bis-(3-aminopropyl)-myristylamine were obtained. 1,095 g of this triamine were condensed with 647 g of ethylene oxide. 1,725 g of bis-(3-aminopropyl)-myristylamine ethoxylate (99%) were obtained. 290 g of this ethoxylate and 754 g of water were reacted with 116.5 g of sodium chloroacetate. The bis-betaine was obtained in 1,160 g of a 30% strength aqueous solution.

EXAMPLE 4

1,056.0 g of octylamine were reacted at 75° C. with 849.6 g of acrylonitrile in 106 g of water, 53 g of methanol and 21.1 g of concentrated acetic acid. 1,810 g of octylaminodipropionitrile were obtained. 1,980 g of the dipropionitrile were hydrogenated in the manner of Example 1 using a cobalt catalyst. 1,970 g of bis-(3-aminopropyl)-octylamine were obtained. 998 g of this triamine were condensed with 845 g of ethylene oxide. 1,840 g of bis-(3-aminopropyl)-octylamine ethoxylate (99%) were obtained. 230 g of this ethoxylate and 613 g of water were reacted with 116.5 g of sodium chloroacetate. The bis-betaine was obtained in 960 g of a 30% strength aqueous solution.

EXAMPLE 5

929 g of tallow fatty amine were reacted at 75° C. with 373 g of acrylonitrile in 68 g of water, 34 g of methanol and 14 g of concentrated acetic acid. 1,237 g of tallow-fatty-aminodipropionitrile were obtained and hydrogenated in accordance with Example 1 to give the corresponding amine.

The ethoxylation reaction was carried out in two stages. First, the bis-(3-aminopropyl)-tallow fatty amine were reacted with 4.7 moles of ethylene oxide using the method of Example 1. The product was then reacted with a further 5.3 moles of ethylene oxide in the presence of the customary 0.2% by weight, relative to the amine, of aqueous sodium hydroxide solution (50% strength), so that the total increase in weight corresponded to a condensation product of the triamine with 10 moles of ethylene oxide. 300 g of this ethoxylate and 777 g of water were reacted with 116.5 g of sodium chloroacetate. The bis-betaine was obtained in 1,190 g of a 30% strength aqueous solution.

The analytical data of the bis-betaines according to the invention, and of their precursors, are summarized in Table I.

TABLE I

| Example/ (Alkyl radical) | Alkylamino-dipropio-nitrile | | Bis-(3-aminopropyl)-alkylamine | | | | Ethoxylate | | $\Sigma a + b + c + d$ equivalents of EO* per mole | Bis-betaine | |
|---|---|---|---|---|---|---|---|---|---|---|---|
| | AN | tert. N (%) | AN | prim. N (%) | sec. N (%) | tert. N (%) | AN | tert. N (%) | | Total chlorine % by weight | Ionic chlorine % by weight |
| 1 (coconut) | 34.3 | 94 | 97.3 | 66.2 | 3.3 | 30.5 | 57.5 | >98 | 4.9 | 3.4 | 3.3 |
| 2 (lauryl) | 34.4 | 95 | 97.5 | 65.9 | 2.9 | 31.2 | 58.3 | >98 | 4.7 | 3.4 | 3.3 |
| 3 (myristyl) | 29.2 | 94 | 82.2 | 65.5 | 3.5 | 31.0 | 51.7 | >98 | 4.9 | 3.3 | 3.2 |
| 4 (octyl) | 42.7 | 94 | 120.2 | 65.1 | 3.0 | 31.9 | 65.1 | >98 | 4.8 | 4.1 | 4.0 |
| 5 (tallow fat) | 27.4 | 94 | 78.0 | 66.1 | 2.6 | 31.3 | 50.0 | >98 | 4.9 | 3.2 | 3.1 |

*EO = ethylene oxide

The abovementioned data are determined as follows:

Alkylaminodipropionitrile

The amine number (AN) and the tertiary nitrogen content are determined by titration with 0.1 N $HClO_4$ in glacial acetic acid or acetic anhydride. The amine number is given by $$AN = \frac{ml\ of\ 0.1\ N\ HClO_4}{original\ sample\ weight\ in\ g}$$

Bis-(3-aminopropyl)-alkylamine

The amine number and the distribution of the amine are determined by titration with 0.2 N solution of HCl in isopropanol in an anhydrous medium. The distribution of amine is carried out by blocking the basic amine-nitrogen with salicylaldehyde (primary N) and phenyl isothiocyanate (primary and secondary N) respectively.

Ethoxylate

The amine number and the tertiary nitrogen content are determined by titration with 0.1 N $HClO_4$ in glacial acetic acid or acetic anhydride. The moles of ethylene oxide absorbed are calculated from the amine numbers or from the increase in mass compared to the previous stage.

Bis-betaine

The total chlorine content is determined after a Parr digestion with $Na_2O_2$, and ionic chlorine is determined by Volhard titration.

The application examples which follow illustrate the ways bis-betaines can be used in hair and body cleaning agents. The amounts and percentages in the examples are in each case relative to the weight, unless otherwise stated.

EXAMPLE 1A

| Hair shampoo with softening effect | |
|---|---|
| Bis-betaine of the formula I, prepared according to Example 1 | 15.00% |
| Polyethylene glycol 6000 distearate | 5.20% |
| Perfume oil | 0.30% |
| Formaldehyde | 0.05% |
| Water to | 100.00% |

EXAMPLE 2A

| Hair shampoo with softening effect | |
|---|---|
| Bis-betaine of the formula I, prepared according to Example 2 | 12.00% |
| Hydroxyethyl cellulose ether | 1.40% |
| Perfume oil | 0.30% |
| Formaldehyde | 0.05% |
| Water to | 100.00% |

EXAMPLE 3A

| Acidic shampoo | |
|---|---|
| Bis-betaine of the formula I, prepared according to Example 1 | 15.00% |
| Citric acid | 0.30% |
| Perfume oil | 0.10% |
| Preservatives, dyestuffs, water to | 100.00% |

EXAMPLE 4A

| Shampoo for damaged hair | |
|---|---|
| Bis-betaine of the formula I, prepared according to Example 2 | 10.00% |
| Sodium salt of lauryltriglycol ether sulfate | 4.00% |
| Coconut-fatty-acid-diethanolamide | 2.00% |
| Sodium chloride | 3.20% |
| Water, preservatives, dyestuffs to | 100.00% |

EXAMPLE 5A

| Anti-dandruff shampoo | |
|---|---|
| Bis-betaine of the formula I, prepared according to Example 2 | 5.00% |
| Sodium salt of palm kernal fatty acid methyltauride | 6.00% |
| Sodium salt of stearic acid methyltauride | 4.00% |
| Sodium salt of laurylsarcoside | 2.00% |
| Zinc salt of 2-mercaptopyridine-N—oxide | 0.50% |
| Perfume oil | 0.20% |
| Water, dyestuffs to | 100.00% |

EXAMPLE 6A

| Shampoo for greasy hair | |
|---|---|
| Bis-betaine of the formula I, prepared according to Example 2 | 7.00% |
| Sodium salt of secondary alkanesulfonate (alkane radical: $C_{13}$–$C_{17}$) | 5.00% |
| α-Olefinsulfonate ($C_{14}$–$C_{16}$) | 2.00% |
| Sodium salt of lauryl sulfate | 2.00% |

-continued

| Shampoo for greasy hair | | |
|---|---|---|
| Water, preservatives, dyestuffs | to | 100.00% |

EXAMPLE 7A

| Shampoo for dry hair | | |
|---|---|---|
| Bis-betaine of the formula I, prepared according to Example 2 | | 10.00% |
| Lauryldimethylamine oxide | | 5.00% |
| Ethylene glycol monostearate | | 1.20% |
| Triethanolamine salt of acylaminotriglycol ether sulfate (acyl = caprylic to stearic acid radical) | | 4.00% |
| Cellulose ether | | 1.40 |
| Water, preservatives, dyestuffs | to | 100.00% |

EXAMPLE 8A

| Shower bath | | |
|---|---|---|
| Bis-betaine of the formula I, prepared according to Example 2 | | 12.00% |
| Disodium salt of lauryltetraglycol ether sulfosuccinate | | 3.00% |
| Hydroxyethylcellulose ether | | 1.20% |
| Perfume oil | | 0.10% |
| Coconut fatty acid monoethanolamide | | 0.80% |
| Water, preservatives, dyestuffs | to | 100.00% |

EXAMPLE 9A

| Foam bath | | |
|---|---|---|
| Bis-betaine of the formula I, prepared according to Example 2 | | 5.00% |
| Sodium salt of lauryldiglycol ether sulfate | | 20.00% |
| Sodium salt of secondary alkanesulfonate (alkane radical: $C_{13}$-$C_{17}$) | | 5.00% |
| Coconut fatty acid diethanolamide | | 2.00% |
| Perfume oil | | 0.40 |
| Sodium chloride | | 3.00% |
| Water, preservatives, dyestuffs | to | 100.00% |

EXAMPLE 10A

| Hand wash | | |
|---|---|---|
| Bis-betaine of the formula I, prepared according to Example 2 | | 10.00% |
| Sodium salt of lauryl sulfate | | 2.00% |
| Sodium salt of lauroylsarcoside | | 4.00% |
| Lactic acid | | 0.10% |
| Water, preservatives, dyestuffs | to | 100.00% |

EXAMPLE 11A

| Foot wash | | |
|---|---|---|
| Bis-betaine of the formula I, prepared according to Example 1 | | 12.00% |
| Coconut-betaine | | 2.00% |
| Coconut dimethylamine oxide | | 2.00% |
| Salicylic acid | | 0.50% |
| Water, perfume oil, dyestuffs | to | 100.00% |

EXAMPLE 12A

| Intimate wash | | |
|---|---|---|
| Bis-betaine of the formula I, prepared according to Example 1 | | 7.00% |
| Coconut-ethylcycloimidino-1-hydroxy-3-ethyl sodium alcholate 2-methyl sodium carboxylate | | 7.00% |
| Triethanolamine salt of lauryltriglycol ether sulfate | | 4.00% |
| Citric acid | | 0.10% |
| 3,4,4'-Trichlorocarbanilide | | 0.20% |
| Water, preservatives, dyestuffs | to | 100.00% |

In the comparative experiments which follow the bis-betaine prepared according to Example 2 was compared with customary anionic surfactants. The conditioning effect was tested not only in vitro but also in vivo, using the following test methods:

1. In vitro test/hair combability 15 cm long middle-European hair strands having a diameter of 1.5 cm were washed in each case with an aqueous solution containing 15% of the surfactant under test. The hair was then rinsed for 2 minutes with tapwater of +35° C. and the combability of the wet hair was assessed. After the test hair had dried, the so-called dry combability, the antistatic action and the wet combability were tested. The results are summarized in Table II.

2. In vivo test/half-head hair combability

The hair of 5 female test persons was in each case parted in the middle and wetted with 100 ml of tapwater of +35° C. Each half of the head was then washed with 5 ml of a 15% strength surfactant-containing solution, foaming being effected for 90 seconds by means of synchronous movements. The hair was then rinsed continuously for 3 minutes with tapwater of +35° C., and the combability of the wet hair was tested and compared using defined polyamide combs. The handle of the wet hair was assessed by neutral test persons. After the hair had dried for 15 minutes, the combability of the dry hair was assessed again by neutral test persons and, at the same time, the handle of the dry hair and the antistatic effect were examined. The results can be seen in Table III.

As the results summarized in Tables II and III show, it is possible to use bis-betaines according to the invention to formulate hair washes which are characterized in particular by a remarkably good softening effect; this means for the use in practice that the hair shampoos make it considerably easier for the consumer to comb wet and dry hair and, in addition, favorably affect the handle of the hair after the application. On using the bis-betaines in body cleaning agents an improvement in the way the skin feels after the application has been found in particular. The examination was carried out in vivo using the following test:

Neutral test persons spread 5 ml of a mixture of 50% of olive oil and 50% of paraffin oil on the hand surfaces. The hands were then washed under running tapwater of +25° C. for 3 minutes with 10 ml of a 15% strength surfactant-containing aqueous solution. In addition to an assessment of the foam appearance in the cleaning effect, a statement was made about how the skin feels immediately after drying and after 10 minutes. The individual results are summarized in Table IV.

TABLE II

| Surfactant | Wet combability | Dry combability | Antistatic properties |
| --- | --- | --- | --- |
| Bis-betaine of Example 2 (according to the invention) | very good | very good | good |
| Triethanolamine salt of lauryl-sulfate (comparison) | poor | poor | poor |
| Sodium salt of lauryldiglycol ether sulfate (comparison) | very poor | moderate | poor |

TABLE III

| Surfactant | Wet combability | Handle of the hair wet | Handle of the hair dry | Dry combability | Antistatic properties |
| --- | --- | --- | --- | --- | --- |
| Bis-betaine of Example 2 (according to the invention) | very good | smooth, pleasant | soft | very good | very good |
| Triethanolamine salt of lauryl-sulfate (comparison) | poor | rough, "braking" | brittle | poor | poor |
| Sodium salt of lauryldiglycol ether sulfate (comparison) | very poor | poor | hard, rough | moderate | poor |

TABLE IV

| Surfactant | How the skin feels on washing | Foam structure | How the skin feels immediately after drying | How the skin feels after 10 minutes |
| --- | --- | --- | --- | --- |
| Bis-betaine Example 2 (according to the invention) | pleasant | creamy, fine-bubbled | pleasant, supple | soft, pleasant |
| Sodium salt of lauryl-sulfate (comparison) | moderate | coarse-bubbled, thin | sticky | very dry, taut |
| Sodium salt of lauryltriglycol ether sulfate (comparison) | moderate | coarse-bubbled | sticky | dry, taut |

We claim:

1. A bis-betaine of the formula

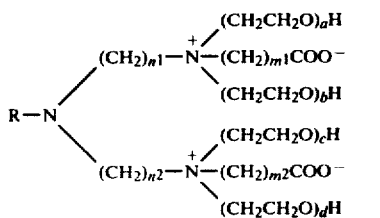

in which

R denotes a saturated or an olefinically unsaturated hydrocarbon radical which has 1 to 3 double bonds and 8 to 22 carbon atoms, $n^1$ and $n^2$ represent an integer from 2 to 3, and $n^1$ and $n^2$ can be identical or different, $m^1$ and $m^2$ represent an integer from 1 to 4, and $m^1$ and $m^2$ can be identical or different, and a, b, c and d, which are identical or different, each is a number from 1 to 5, with the proviso that the sum (a+b+c+d) should be at most 10.

2. A process for preparing a bis-betaine as claimed in claim 1, in which a primary amine of the formula $RNH_2$ (II) is first reacted with 2 moles of at least one reactive nitrile of 2 to 3 carbon atoms to give a compound of the formula

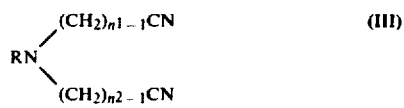

which is reduced in the presence of hydrogen to give a compound of the formula

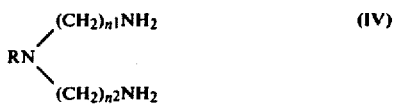

which is condensed with ethylene oxide to give a compound of the formula

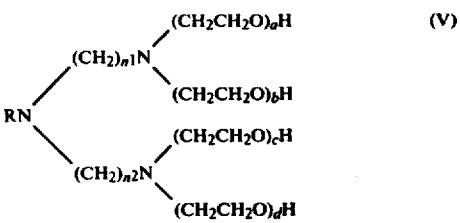

which process comprises quaternizing this compound of the formula (V) in an aqueous solution with at least one alkali metal salt of an ω-halocarboxylic acid of the formula $$X(CH_2)_m{}^1(m^2)COOH$$

3. A cosmetic cleaning agent, containing water as a liquid carrier, at least one surfactant from the group consisting of anionic, cationic, non-ionic and amphoteric surfactants, customary cosmetic additives and auxiliaries, which comprises a surface active effective amount of a bis-betaine as claimed in claim 1.

4. An industrial cleaning agent, containing water as a liquid carrier, at least one surfactant from the group consisting of anionic, cationic, non-ionic and amphoteric surfactants and, cleaning-promoting additives and customary auxiliaries, which comprises a surface active effective amount of a bis-betaine as claimed in claim 1.

* * * * *